United States Patent [19]

Yang et al.

[11] Patent Number: 5,071,952

[45] Date of Patent: Dec. 10, 1991

[54] (IODO-UREA AND IODO-ISOCYANO) DIOXEPANE TRIOXANE COPOLYMERS

[75] Inventors: Nan-Loh Yang, Staten Island, N.Y.; Andrew Auerbach, Livingston; James L. Paul, Summit, both of N.J.; Rose Pesce, College Point, N.Y.

[73] Assignee: Hoechst Celanese Corporation, Chatham, N.J.

[21] Appl. No.: 181,236

[22] Filed: Apr. 13, 1988

[51] Int. Cl.$^5$ .......................... C08G 2/24; C08G 2/26; C08G 2/30

[52] U.S. Cl. ..................................... 528/249; 525/410; 525/411

[58] Field of Search .......................... 528/249; 525/410

[56] References Cited

U.S. PATENT DOCUMENTS

| | | | |
|---|---|---|---|
| 3,297,647 | 1/1967 | Schott et al. | 528/241 |
| 3,337,587 | 8/1967 | Tinsley | 549/337 |
| 3,385,832 | 5/1968 | Jennings et al. | 528/246 |
| 3,457,233 | 7/1969 | Ishida et al. | 525/410 |

FOREIGN PATENT DOCUMENTS

| | | | |
|---|---|---|---|
| 720516 | 10/1965 | Canada . | |
| 1196374 | 7/1965 | Fed. Rep. of Germany . | |
| 2062958 | 7/1970 | Fed. Rep. of Germany . | |
| 43-23471 | 9/1968 | Japan | 528/249 |
| 0046793 | 11/1972 | Japan | 525/410 |

OTHER PUBLICATIONS

R. C. Schulz, Makaromol. Chem. Suppl. 12, 1–9 (1985).
R. C. Schulz, Makromol. Chem. Suppl. 13, 123–136 (1985).
W. Hellermann and R. C. Schulz, Makromol. Chem., Rapid Commun. 2, 585–589 (1981).
K. C. Brannock and G. R. Lappin, J. Organic Chem., 21, 1366–1368 (1956).
R. R. Wittekind, J. D. Rosenau and G. I. Poos, J. Organic Chem. 26, 444–446 (1961).
L. Birckenbach and M. Linhard, Ber., 64, 1081–1087 (1931).
C. G. Gebelein, J. Macromol, Sci–Chem., A5(2) 433–432 (1971).
P. H. Plesch and P. H. Westermann, Polymer, 10, 105 (1965).
E. J. Vandenberg, J. of Polymer Sci. Polymer Chem. Ed., 23, 951–970 (1985).
S. Penczek, P. Kubisa and V. Matyjaszewski, Adv. Polymer Sci. 68/69 Cationic Ring Opening Polymerization, 2. Synthetic Applications p. 91 (1981).

*Primary Examiner*—John Kight
*Assistant Examiner*—Frederick Krass
*Attorney, Agent, or Firm*—Dimitrios T. Drivas

[57] ABSTRACT

Iodoisocyano, iodourea and oxazole modified 1,3 diox-ep-5-ene ring monomers are synthesized and used in copolymerization reactions with trioxane to produce acetal copolymers with backbone functional groups. The invention also concerns processes for the production of acetal copolymers containing iodourea and oxazole functional groups from acetal copolymers with backbone double bonds.

3 Claims, No Drawings

(IODO-UREA AND IODO-ISOCYANO) DIOXEPANE TRIOXANE COPOLYMERS

BACKGROUND OF THE INVENTION

Polyacetal copolymers are technically important macromolecules competitive with metals, ceramics and nylons in many applications. In the current technical processes, they are prepared by copolymerization of trioxane with a comonomer such as ethylene oxide, dioxolane or butanediol formal. Each such copolymer molecule carries a maximum of two functional groups, e.g. hydroxyl end groups. For purposes such as the preparation of graft copolymers and polymers with chemically bound stablizers, it is desirable to synthesize polyacetals with higher levels of functional groups. It is an object of this invention to prepare polyacetal copolymers of trioxane that have stability equivalent to or greater than that of conventional resins while at the same time having functional groups which may be useful for further modifications or the attachment of additives.

In conventional acetal resin products, additives such as amidine thermal stabilizers and the like tend to reside in the amorphous regions of the polymer. Since the distribution of such non-crystalline areas is spatially random, the distribution of additives is often not optimal in terms of macroscopic properties. If functional sites can be provided at regular or semi-regular intervals (e.g. random copolymer) such that stabilizers or impact modifiers could be attached at a predetermined locus of points within the resin, then superior and more uniform properties could be achieved. This approach is particularly advantageous since the crystal structure of polyacetal is such that additives may be sterically obstructed from the crystalline areas. It therefore may be desirable to provide polymer backbone moieties that may disrupt the polymer's crystal structure in a controlled manner and provide a locus for attachment of additives.

Polyacetal copolymers with such backbone functional groups would be useful in many important applications such as: a) preparing trioxane copolymers with chemically bonded stabilizers; b) preparing trioxane copolymers with chemically attached impact modifiers; c) preparing grafted copolymers of trioxane as compatibilizers with existing commercial acetal copolymer blends or with other polymer materials such as glass or minerals; d) preparing copolymers amenable to surface modifications; and e) preparing crosslinked copolymers.

SUMMARY OF THE INVENTION

The present invention concerns the production of 5-iodo-6-isocyano-1,3-dioxepane, 5-iodo-6-urea-1,3-dioxepane and 5,6-oxazole-1,3-dioxepane and the use of these comonomers in polymerizations with trioxane to produce acetal copolymers with backbone functional groups.

The invention also concerns processes for the production of acetal copolymers with iodourea and oxazole functional groups from TX-DXPE acetal copolymers produced by copolymerizing trioxane and 1,3-dioxep-5-ene. The modifications of the copolymer backbone double bonds on the TX-DXPE copolymers are efficiently performed in an acetonitrile solvent system.

DETAILED DESCRIPTION OF THE INVENTION

EXAMPLE 1

Synthesis of monomers

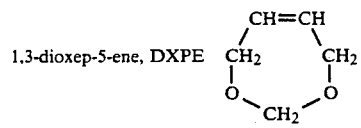

A mixture of 176 g. (2 moles) of cis-2-butene-1,4-diol, 60 g (2 moles) of paraformaldehyde, 25 ml. of benzene and 0.25 g. of p-toluenesulfonic acid was refluxed under a Dean-Stark trap until the removal of water was completed. Distillation of the reaction mixture after the removal of benzene yielded 172 g. of crude 1,3-dioxep-5-ene (b.p. 120°–126° C.). The crude product containing small amounts of water and formaldehyde was purified by redistillation from solid potassium hydroxide. Pure 1,3-dioxep-5-ene (b.p.=130° C.) was obtained in the amount of 160 g.

EXAMPLE 2

Incorporation of Isocyanate Functional Group

Modified Ring Monomer

A modified ring monomer was prepared by reacting 2 g. (0.02 moles) of DXPE with 5 g. (0.02 moles) of iodine, and excess silver cyanate (6 g., 0.04 moles). The product of this reaction was then reacted with excess anhydrous ammonia. The reaction was attempted in two different solvents, ethyl ether and acetonitrile. It was observed that for the reaction run in ether the brown color of the mixture persisted after 5 hours, indicating that all of the iodine had not yet reacted. The mixture was filtered to remove the inorganic salts and anhydrous ammonia was bubbled through the filtrate, resulting in the formation of a yellowish solid. This mixture was then filtered and some product was recovered. It was observed to form a brown viscous liquid on standing.

The proposed structure on the product is

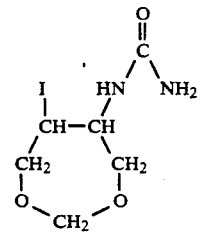

When the reaction was run in acetonitrile, the brown color of the mixture was observed to disappear after several minutes. The yield was substantially higher than that of the reaction in ether. The carbon-13 NMR spectrum of the product was identical to that obtained from the product when ether was used as the solvent for the reaction. The IR spectrum of the product obtained when acetonitrile was used as the solvent was obtained on a Beckman 4260 spectrophotometer. Peaks were observed at 3450, 3350, 3250 and 1560 indicating the presence of an amide, and at 1650 indicating the presence of a carbonyl. Peaks at 2900, 1440 and 1360 (CH) and at 1070-1150 (C—O—C) were also observed.

This 5,iodo,6,urea,1,3-dioxepane monomer was further modified by the application of heat to produce the monomer 5,6-oxazole, 1,3-dioxepane having a proposed formula as follows:

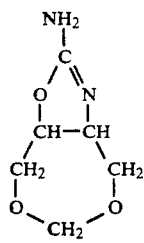

The urea and oxazole modified comoners of this invention synthesized as described above may be used in copolymerization reactions to produce acetal copolymers containing urea and oxazole backbone functional groups respectively.

EXAMPLE 3

Modification of Copolymer Double Bond Through Isocynanate Formation

Copolymerization of Trioxane with 1,3-Dioxep-5-ene

In a dry flask (Kjeldahl, 100 ml) were placed 28.5 g of trioxane and 1.5 g of 1,3-dioxep-5-ene. The flask was capped with a serum stopper. After removing the air and the dissolved gas under vacuum from the reaction mixture, the flask was flushed with nitrogen. The contents were melted and mixed together at a temperature range of 60° to 65° C. with a magnetic stirrer in an oil bath. Then, 2 ul (microliters) of boron trifluoride etherate was injected through the serum stopper into the flask kept in an oil bath at 60° C. The color of the solution immediately became dark brown. Within about several minutes the solution became immobilized by the growth of the polymer throughout the flask. The polymerization was allowed to proceed at 60° C. for 20 hours. At the conclusion of polymerization, the polymer was removed and ground into small chunks. The crude polymer was washed with 60 ml of a methanol solution with 2% triethanolamine and then collected by filtration. The product was about 24 gms. The unstable end groups were removed by base hydrolysis in the following procedure.

Into a 500 ml, two-necked round bottom flask fitted with an air-cooled, straight through condenser, thermometer and magnetic stirrer were placed crude polymer (24 g), DMF (120 ml), Benzyl alcohol (120 ml) and 1% TEA (of total solution volume). The mixture was stirred and heated at 160°-170° C. to dissolve the solids. The contents were maintained at refluxing condition until visible evolution of formaldehyde stored. The polymer solution was cooled down to precipitate out solid material. The solid was removed and washed by acetone three times. The polymer was filtered and dried under vacuum at 40° C. The yield was about 18 gms.

The copolymer's carbon-carbon double bond can provide an excellent site for further modifications which may serve to stabilize the polymer. One such modification is the addition of iodine isocyanate. The addition of iodine isocyanate to the double bond was first attempted in an ether solvent. The IR and carbon-13 NMR spectra of the reaction run in ether show no signs of successful modification. Separation of the copolymer from the inorganic salts in the ether solvent proved to be quite difficult.

This problem was avoided by running the reaction in acetonitrile. Because the reaction of iodine and silver cyanate is very rapid in acetonitrile, it was possible to add the copolymer to a preformed solution of iodine isocyanate. This was done and the mixture was allowed to react for 20 hours. The copolymer was then filtered off and washed four times with acetonitrile. The product of such a modification can then be further reacted with anhydrous ammonia to yield a unit with the structure:

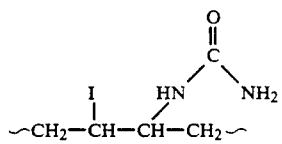

where the urea moiety can act as formaldehyde acceptor. This reaction was carried out by bubbling an excess of anhydrous ammonia through a mixture of the washed copolymer and acetonitrile. The copolymer was then filtered off and again washed four times with acetontrile.

The IR spectrum of the modified copolymer shows the characteristic acetal peaks (2900,1460,1360, 1240, 1100 and 900) cm$^{-1}$ as well as peaks at 1740 (C=O) and 1700 (amide) indicating that the desired modification had been acheived. The proton NMR spectrum of the product shows a peak at 8.1 ppm (NH) which is absent from the spectrum of the unmodified copolymer. The carbon-13 NMR spectrum of the product shows a definite peak at 169 ppm (C=O). No peaks were observed in this area for the unmodified copolymer. The doublet at 68 ppm (CH$_2$—CH=CH—CH$_2$) is still observed in the modified copolymer and was found to have approximately the same intensity as the peak in the unmodified copolymer. On the other hand, the intensity of the peak at 128 ppm (CH$_2$CH=CH—CH$_2$), appears to be smaller than that of the unmodified copolymer, indicating that at least some of the double bonds were modified. It is possible to further modify the iodine and urea substituted unit to yield a polymer having the formula:

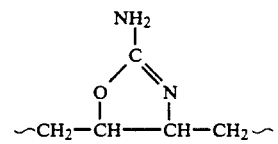

Such a modification of the iodine and urea to an oxazole structure may be accomplished by the application of heat. It would be advantageous to covert the stopper unit of the copolymer to the oxazole structure to remove iodine which may cause polymer degradation. On the other hand, the iodine may also, of course, be used to attach additional functional groups.

What is claimed is:

1. A process for producing an acetal copolymer with backbone urea groups comprising copolymerizing trioxane with 5-iodo-6-urea-1,3-dioxepane.

2. A process for producing an acetal copolymer with iodo and urea backbone groups which comprises:

a) copolymerizing trioxane with 1,3-dioxep-5-ene to produce an acetal copolymer;
b) preparing a first mixture of the copolymer so produced with acetonitrile;
c) introducing iodine and silver cyanate into the first mixture and allowing the first mixture to react for a suitable time period;
d) filtering off the copolymer;
e) preparing a second mixture of the copolymer with acetonitrile; and
f) introducing an excess of anhydrous ammonia into the second mixture and allowing the mixture to react for a suitable time.

3. The acetal copolymer produced by the process of claim 2.

* * * * *